(12) United States Patent
Li et al.

(10) Patent No.: US 6,843,901 B1
(45) Date of Patent: Jan. 18, 2005

(54) POTENTIAL GRADIENT DETECTOR FOR ELECTROPHORESIS

(75) Inventors: Sam Fong Yau Li, Singapore (SG); Hongping Wei, Singapore (SG); Guixin Zhang, Singapore (SG)

(73) Assignee: CE Resources PTE LTD, Singapore (SG)

( * ) Notice: Subject to any disclaimer, the term of this patent is extended or adjusted under 35 U.S.C. 154(b) by 397 days.

(21) Appl. No.: 09/980,361

(22) PCT Filed: Jun. 1, 2000

(86) PCT No.: PCT/SG00/00077
§ 371 (c)(1),
(2), (4) Date: Apr. 9, 2002

(87) PCT Pub. No.: WO00/75650
PCT Pub. Date: Dec. 14, 2000

(30) Foreign Application Priority Data

Jun. 4, 1999 (SG) .......................................... 9902707-0

(51) Int. Cl.⁷ .......................................... G01N 27/447
(52) U.S. Cl. .................................... 204/603; 204/452
(58) Field of Search ............................ 204/451–455, 204/601–605

(56) References Cited

U.S. PATENT DOCUMENTS

| | | | | |
|---|---|---|---|---|
| 5,169,510 A | * | 12/1992 | Lunte et al. ................. | 204/601 |
| 5,441,613 A | * | 8/1995 | McCormick et al. ........ | 204/452 |
| RE35,102 E | * | 11/1995 | Zare et al. ................... | 204/453 |
| 5,580,435 A | * | 12/1996 | Kovacs ........................ | 204/603 |
| 5,906,723 A | * | 5/1999 | Mathies et al. ............. | 204/603 |

FOREIGN PATENT DOCUMENTS

JP   1108890 A  * 4/1999  ......... G01N/27/447

OTHER PUBLICATIONS

R.A. Wallingford and A.G. Ewing, "Capillary Zone Electrophoresis with Electrochemical Detection", Anal. Chem. 1987, 59, 1762–1766.*

* cited by examiner

*Primary Examiner*—Nam Nguyen
*Assistant Examiner*—Jeffrey Barton
(74) *Attorney, Agent, or Firm*—Lawrence Y.D. Ho & Assoc's.

(57) ABSTRACT

An on-column detector for electrophoresis samples based on the principles of potential gradient detection, in which the electrodes for detection are physically isolated from the electrophoretic separation process, but maintains the same electrical potential as the corresponding interior of the electrophoretic separation channel. Potential gradient detection is used to measure the applied electrical field at two points within the electrophoretic channel during electrophoresis. When sample components with conductivity different from the electrophoretic medium passes between these two points, it causes a change in the potential gradient between the two points, which would be sensed by the sensing electrodes of the detector and registered by a data acquisition system. The apparatus can make use of conventional separation channel as well as separation channels on microchips. In accordance with the present invention, a sensor with electrically conductive medium is added and connected to the separation channel via a conductive element on the surface of the separation channel.

27 Claims, 8 Drawing Sheets

POTENTIAL GRADIENT DETECTOR FOR ELECTROPHORESIS

FIELD OF THE INVENTION

The present invention is related to sample detection in electrophoresis. In particular, the present invention is related to conductivity detection in electrophoresis.

BACKGROUND OF THE INVENTION

Capillary electrophoresis (CE) is a powerful analytical separation technique for the analysis of complex mixtures. In CE, an unknown sample is introduced at an Inlet of a capillary channel filled with a buffer solution, and a high voltage is applied across a section of the capillary. Different constituents of the sample migrate through the capillary at different rates depending on their electrophoretic mobility's, and are separated into different zones. By detecting the chemicals passing through a part of the capillary or its outlet as a function of time, and knowing the of the possible constituents, the chemical composition of the sample can be determined. A number of detectors have been developed for CE, including optical and electrochemical methods. Electrochemical detection can be classified into three main categories: amperometry, voltammetry and conductivity measurements. Conductivity detection is a non-selective detection mode and universally applicable. Analytes are detected because of their different conductivities to that of the background electrolyte.

One method to measure conductivity during electrophoresis is potential gradient detection, which is accomplished by putting two electrodes in the applied electric field for electrophoresis and detecting sample components by measuring potential changes between these two electrodes when sample components are passing by. This method has been used for isotachophoresis (U.S. Pat. No. 3,941,678, 20 Feb. 1975 and U.S. Pat. No. 3,932,264, 13 Jan. 1976) and it has been mentioned that such a method can be used in modem CE (F. Foret, L. Krivankova and P. Bocek, Capillary Zone Electrophoresis, chapter 7, p147–150). There are, however, problems for using this method in electrophoresis. Firstly, the sensing electrodes need to be inserted into the separation column or capillary. The procedures are troublesome and tedious, especially if the inner diameter of the capillary is small, for example in the case of capillary electrophoresis (usually between 10–100 $\mu$m). The more serious problem is that the sensing electrodes are polarized during electrophoresis. In order to prevent formation of bubbles and deposits on the electrodes so that the electrophoresis processes can be performed under stable conditions and high sensitivity can be obtained, special means have to be used, such as adopting v/F and F/v converters in the instrumental design, reducing the areas of electrodes contacting with the buffer solutions and adding nonionic surfactant. However, all these means can only serve to alleviate, but can't eliminate completely the problems encountered.

Therefore, conductivity detection is usually accomplished by measuring the potential difference (signal) between two electrodes while passing through a small constant current (excited source). Several designs are used for conductivity detection in CE, i.e., on-column, end-column and contactless structures. On-column detection cells (Anal. Chem., 1987, 59, 2747–2749, U.S. Pat. No. 5,223,114, 29 Jun. 1993 and U.S. Pat. No. 5,580,435, 1994) are usually made by inserting two sensing platinum wires into the separation capillary so that the sensing electrodes can directly contact the electrolyte solution in the capillary. Although on-column conductometric detection works well, the question arises as to how to produce such structures reliably and inexpensively. The more common practices are the use of end-column detectors (such as those disclosed in Anal. Chem. 1991, 63, 189–192, J. of Capillary Electrophoresis, 1996, 1:1–11, U.S. Pat. Nos. 5,298,139, and 5,126,023), which have the advantage that the sensing electrode can be constructed directly at the outlet of the separation capillary. For end-column detection, the correct alignment of the sensing electrode with the outlet of the separation capillary is critical for success. However, the alignment is usually difficult due to the small inner diameter (10 $\mu$m–100 $\mu$m) of the capillary.

Another solution offered in the prior art is contactless conductivity detection (Anal. Chem., 1998, 70, 563–567). In this method, two electrodes are laid on the outside wall of the separation capillary. Therefore, no electrode is in contact with electrolyte solution. However, it is generally accepted that the contactless detection is not sensitive enough. Although their structures are varied, all the prior designs should use their own excited source and considered the high voltage applied for electrophoresis as a noise source.

Although the three techniques described above (i.e. potential gradient detection, potential difference detection, and contactless conductivity detection) are all based on the difference in conductivity between the electrophoretic medium and the samples, potential difference detection is the most widely used technique in capillary electrophoresis. Therefore, commercially available and commonly described conductivity detection systems typically employ the potential difference detection method.

OBJECT OF THE INVENTION

It is therefore an object of the present invention to provide a conductivity detection system which obviates the need to insert electrodes into the separation channel.

It is another object to provide a conductivity detection system which is effective and sensitive.

SUMMARY OF THE INVENTION

The present invention provides an on-column electrochemical detector based on the principle of potential gradient detection for electrophoresis of samples in which the electrodes for detection are physically isolated from the electrophoretic separation channel, but maintain the same electrical potential as the corresponding interior of the electrophoretic separation channel. Since the sensing electrodes are not in direct contact with the electrophoretic medium within the electrophoretic channel, problems due to bubble and deposit formation are eliminated.

The apparatus can make use of conventional separation channel with an inlet end connected to an inlet reservoir and an outlet end connected to an outlet reservoir. In accordance with the present invention, a sensor reservoir with electrically conductive medium is added and connected to the separation channel via a conductive element on the surface of the separation channel. A sensing electrode is submerged in the electrically conductive medium within the sensing reservoir. The conductive element allows electrical potential from the interior of the separation channel to be transferred to the sensor reservoir without detectable bulk flow of electrophoretic medium or samples. Detectable bulk flow refers to the movement of solute or sample to an extent that there is detectable interference or disruption to migration of the sample. This detection may be based standard detection methods or the method described in the present invention. In one embodiment, the conductive element is a fracture in a separation channel made of fused silica tubing. In another embodiment, the conductive element is a thin layer of porous glass on the wall of a capillary channel electrophoretic chip.

During electrophoresis, the channel and reservoirs are filled with electrophoretic medium, and the ground and power electrodes from a power supply are connected to the outlet and inlet reservoirs respectively. Sample detection is achieved by sensing the potential gradient between the conductive element and the outlet end where the sensing and reference electrodes are respectively connected in the preferred embodiment. The distance between the element and the outlet end is also preferably as small as the length of the sample plug in order to maximize sensitivity of detection and resolution.

DESCRIPTION OF THE INVENTION

The following detailed description describes the preferred embodiment for implementing the underlying principles of the present invention. One skilled in the art should understand, however, that the following description is meant to be illustrative of the present invention, and should not be construed as limiting the principles discussed herein. In addition, certain terms are used throughout the following description and claims to refer to particular system components. As one skilled in the art will appreciate, companies may refer to a component by different names. This document does not intend to distinguish between components that differ in name but not in function. For example, the pair of electrodes for electrophoresis are referred to herein as "ground" and "power" electrodes for clarity of description. It is understood by one skilled in the art that the ground electrode may be at zero volts or floating, and that the power electrode may be of positive or negative polarity. For the same reason of clarity of description, the pair of electrodes for potential gradient detection are referred to herein as "sensing" and "reference" electrodes. It should be understood that the "sensing" electrode could be the same type as the "reference" electrode. Their positions can be exchanged with each other without affecting detection results. When performing electrophoresis on microchip, at least four electrodes are often needed for sample introduction and separation. For ease of understanding, these electrodes are classified as "power", "ground", "sample" and "waste" electrodes. It should be understood that the exact potential on these electrodes are not fixed, and may be set up according to the needs of the user. The reservoirs on the microchip have also been given the names "inlet", "outlet", "sample" and "waste" reservoirs for clarity of description. It should also be understood that the reservoirs can be used to contain different medium depending on the experimental conditions required. Furthermore, no particular inlet and outlet reservoir structures are required if microinstruments are used to load small quantities of samples directly into the inlet end.

In the following discussion, and in the claims the terms "including", "having" and "comprising" are used in an open-ended fashion, and thus should be interpreted to mean "including but not limited to . . . ". Also, the term" or "couples" is intended to mean either an indirect or direct electrical connection. Thus if a first device "couples" to a second devices, that connection may be a direct electrical connection or through an indirect electrical connection via other devices, electrical conductive medium or connections. Capillary electrophoresis is used for purposes of illustration. It should be understood by one skilled in the art that the same principles may be applied to other types of electrophoretic separations, using the teaching provided herewith.

Figures 1A, 1B:
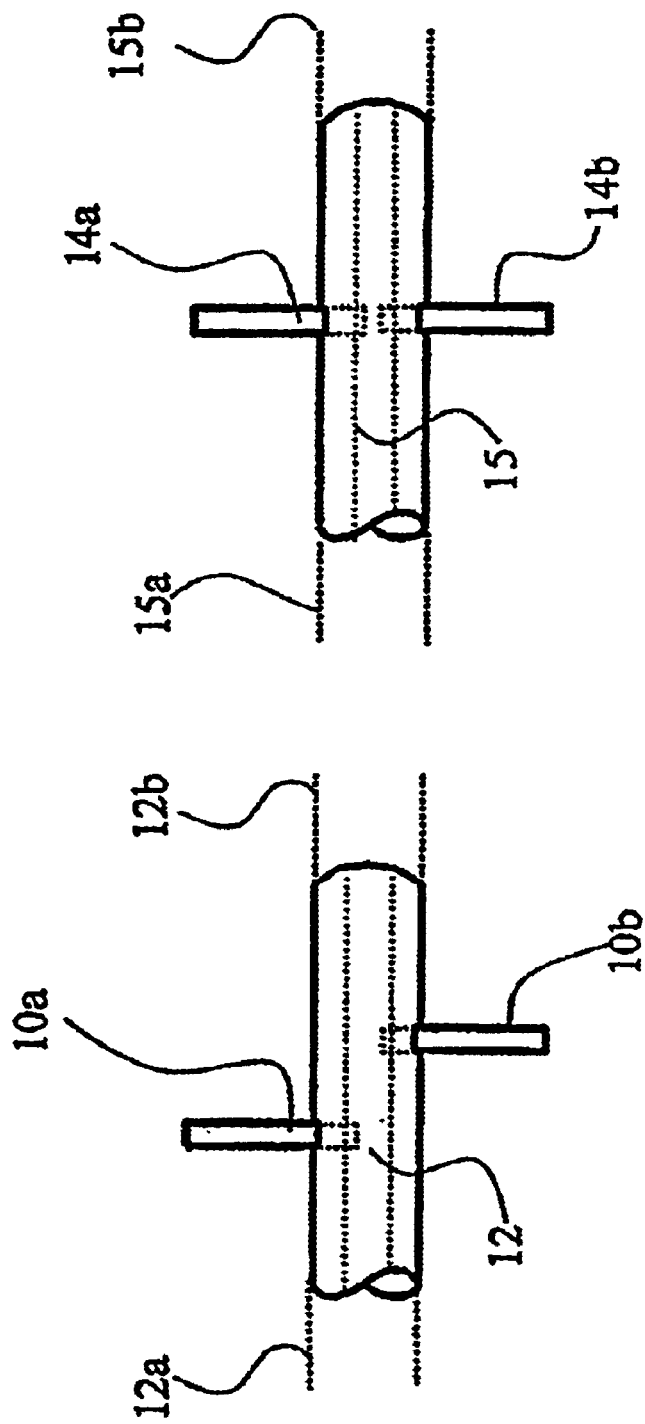
FIGS. 1A and B are typical detection methods described in the prior art.

FIGS. 1A and B show a section of an electrophoretic capillary tube, illustrating the principles of potential gradient and potential difference detection systems respectively as known in the art. In the potential gradient detection system as shown in FIG. 1A, the two sensing electrodes 10A and 10B come into contact with the electrophoretic medium at two non-parallel positions along the longitudinal axis of the electrophoretic channel 12, which is connected to a power source generating an electrical potential between ends 12a and 12b. The portions of the electrodes in contact with the solution inside the capillary tube is shown in dotted lines. In the potential difference detection method, the two sensing electrodes 14A and 14B have to be in contact with the electrophoretic medium at exactly the same cross-sectional plane of channel 15 having an electrophoretic potential between ends 15a and 15b. The resistance of the electrophretic medium may be monitored using a small a.c. current between the sensing electrodes. Because the sensing electrodes are within high electric field during electrophoresis, bubble and deposit form on the surface of the sensing electrodes due to electrochemical reactions, which would affect the electrophoretic process, and decrease the detection sensitivity since the sensing electrodes are directly within the electrophoretic channel.

Figure 2A:
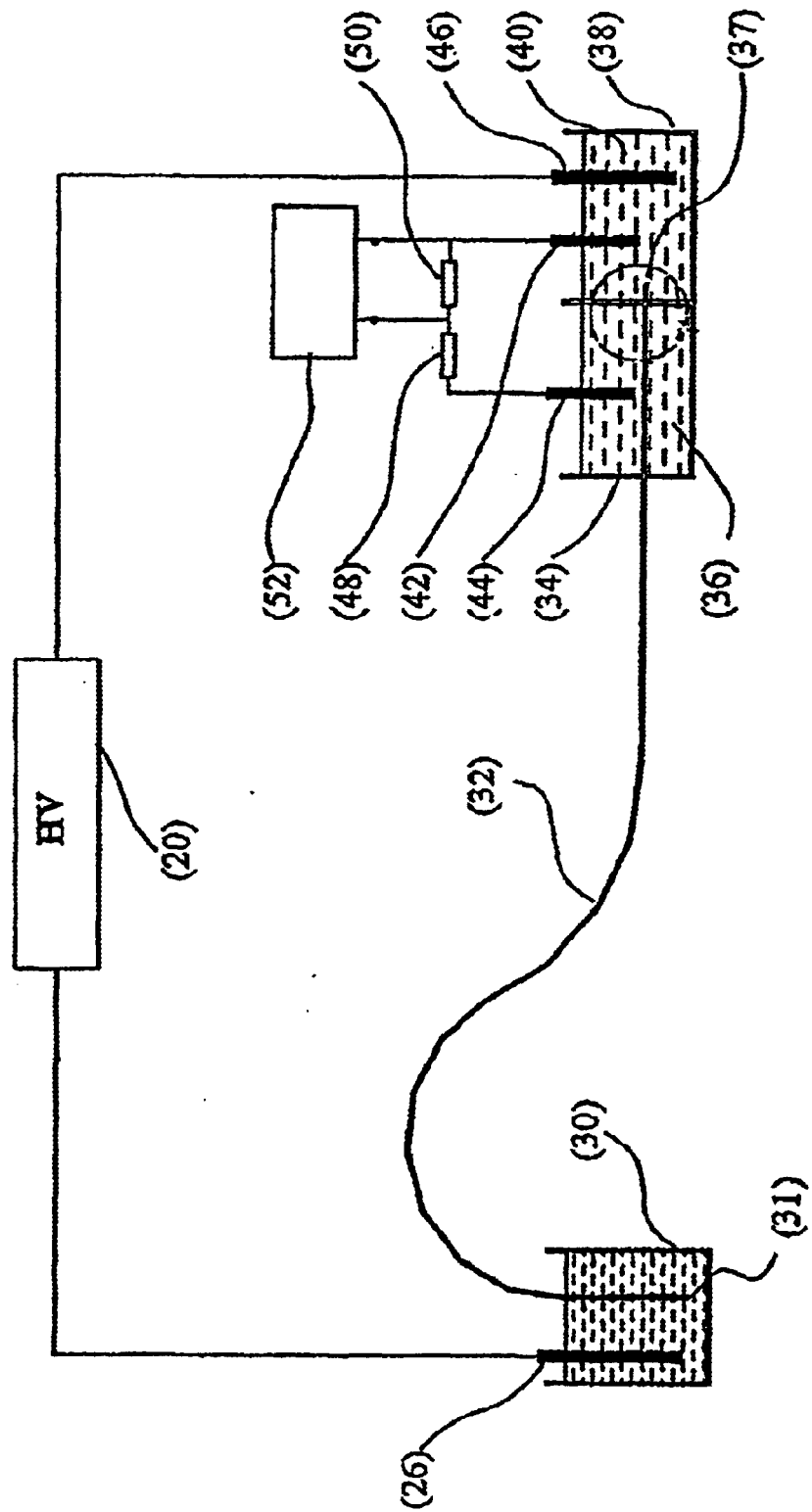
FIG. 2A is a schematic diagram of a capillary electrophoresis system as described in one embodiment of the present invention.
Figure 2B:
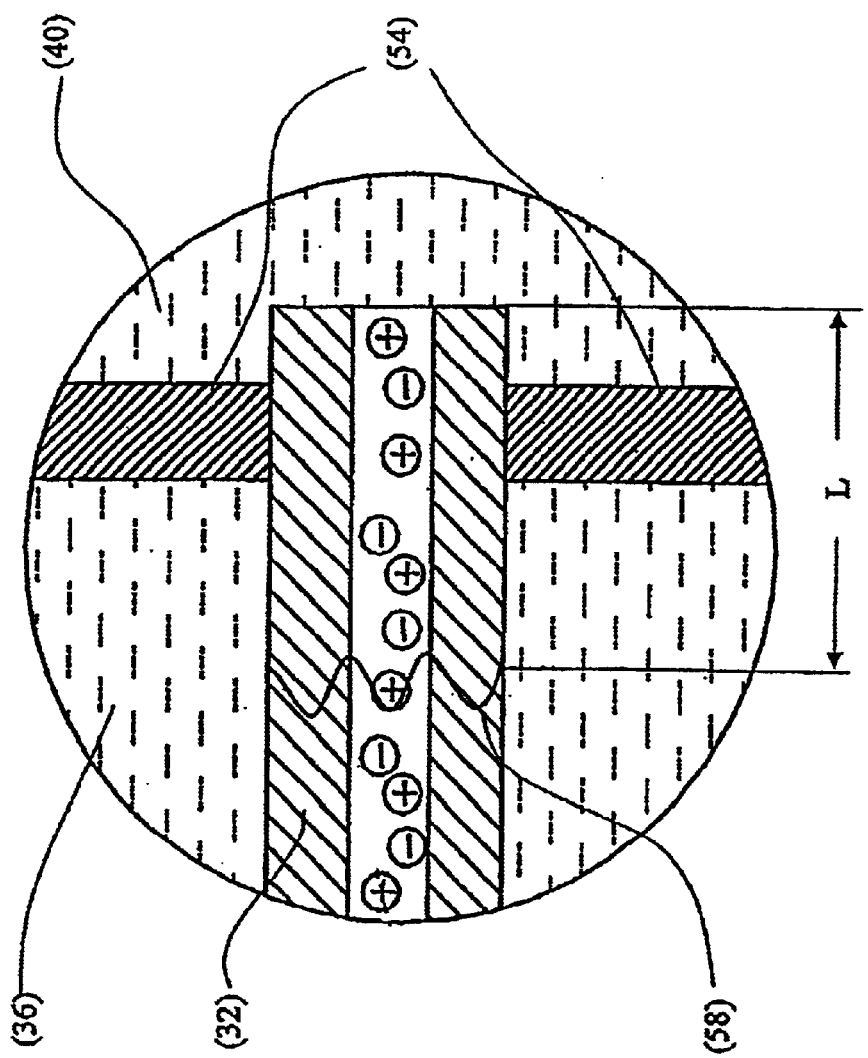
FIG. 2B is an enlarged view of area G as shown in FIG. 2A.

FIGS. 2A and 2B show one setup of capillary electrophoresis (CE) based on potential gradient detection constructed in accordance with the present invention. A 50 µm inner diameter fused silica capillary is used as the separation capillary 32. A fracture 58 is made before the outlet of the separation capillary 32. The distance L between the fracture 58 to the outlet, usually between 0.1 mm to 5 mm, should be near or smaller than the length of the sample plug injected into the separation capillary 32 in order to obtain maximum resolution between separated peaks. The capillary 32 is then inserted into the buffer reservoirs so that the outlet 37 of the capillary is connected to outlet reservoir 38, fracture 58 is submerged in sensor reservoir 34, and inlet 31 of the capillary is inserted into inlet reservoir 30. Good insulation between reservoirs 34 and 38 is made by using an insulation layer 54. Running buffer solutions for electrophoresis are filled into the three buffer reservoirs as well as the bore of the separation capillary 32. The ground and power electrodes 46 and 26 are connected with the high voltage power supply 20 to apply high voltages needed for electrophoresis. Sensing electrode 44 is put in electrically conducting solution 36 contained in sensor reservoir 34, and a reference electrode 42 is put in the solution 40 contained in outlet reservoir 38. Between electrodes 44 and 42, two resistors 48 and 50 are used to sample the potentials between electrodes 44 and 42 to the data acquisition system 52. For sample separation, the sample can be injected by hydrodynamic injection or electrokinetic injection methods into capillary 31, and a high voltage applied between the ground and power electrodes. Sample detection is achieved by sensing the potential difference between the reference electrode 42 and the sensing electrode 44 over time. These techniques are described by S. F. Y. Li in *Capillary electrophoresis: Principles, Practice and Applications,* Elsevier Science Publications, 1992.

Figure 3B:
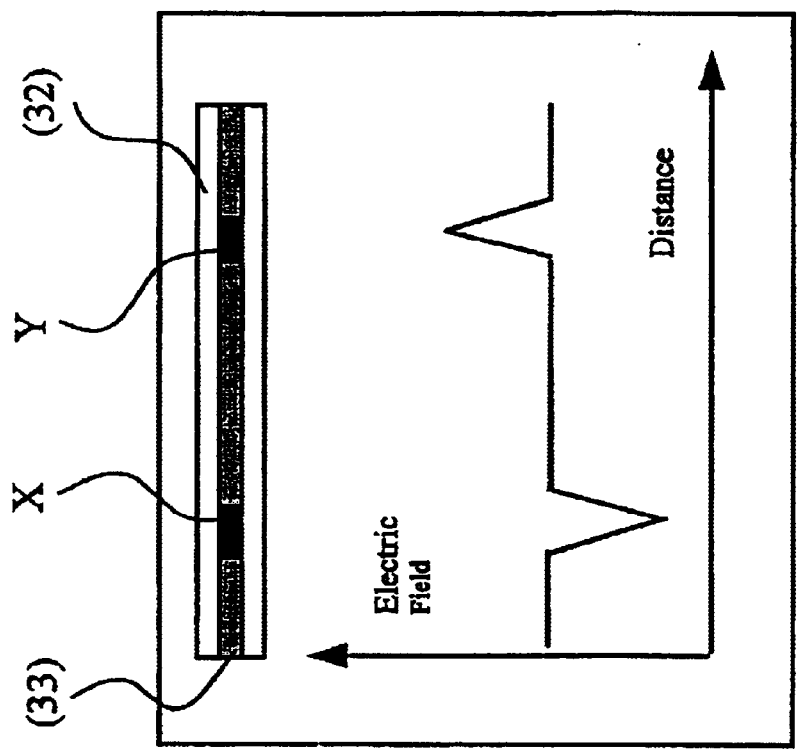
FIG. 3B shows the electric field as detected by the data acquisition system using the capillary electrophoretic system shown in FIG. 2A when sample is injected and separated into zones.
Figure 3A:
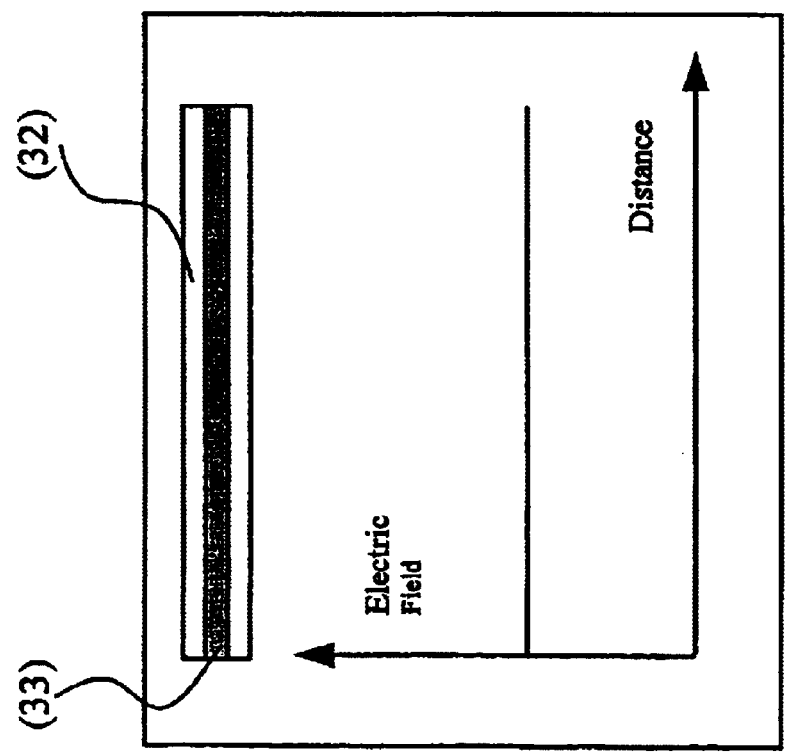
FIG. 3A shows the electric field as detected by the data acquisition system using the capillary electrophoretic system shown in FIG. 2A without sample.

The embodiment shown in the above figures can be used for conductivity detection in many methods of electrophoresis. For simplicity, capillary zone electrophoresis (CZE) is chosen for explaining the principle of the present invention. FIGS. 3A and B show a theoretical electric field across the corresponding section of capillary tube 32. FIG. 3A shows buffer 33 alone. FIG. 3B shows buffer 33 with samples X and Y being separated by CZE. When a high voltage is applied, a straight baseline of electric field across the whole capillary 32 as shown in FIG. 3A is theoretically obtained because the running buffer is homogeneous during CZE. However, some difference in the electric field will exist if a sample is injected into the capillary. If the sample component's mobility, for example X, is larger than that of the running buffer, the electric field in the plug of the sample component will be lower than that of the running buffer as shown in FIG. 3B. Conversely, if the sample component's mobility, for example Y, is smaller than that of the running buffer, the electric field in the plug of the sample component will be larger than that of the running buffer (FIG. 3B). When the sample components are passing by the region between the fracture 58 and the outlet of the capillary, the potential between electrodes 44 and 42 will change and the analytes A or B can be detected.

Figure 4:
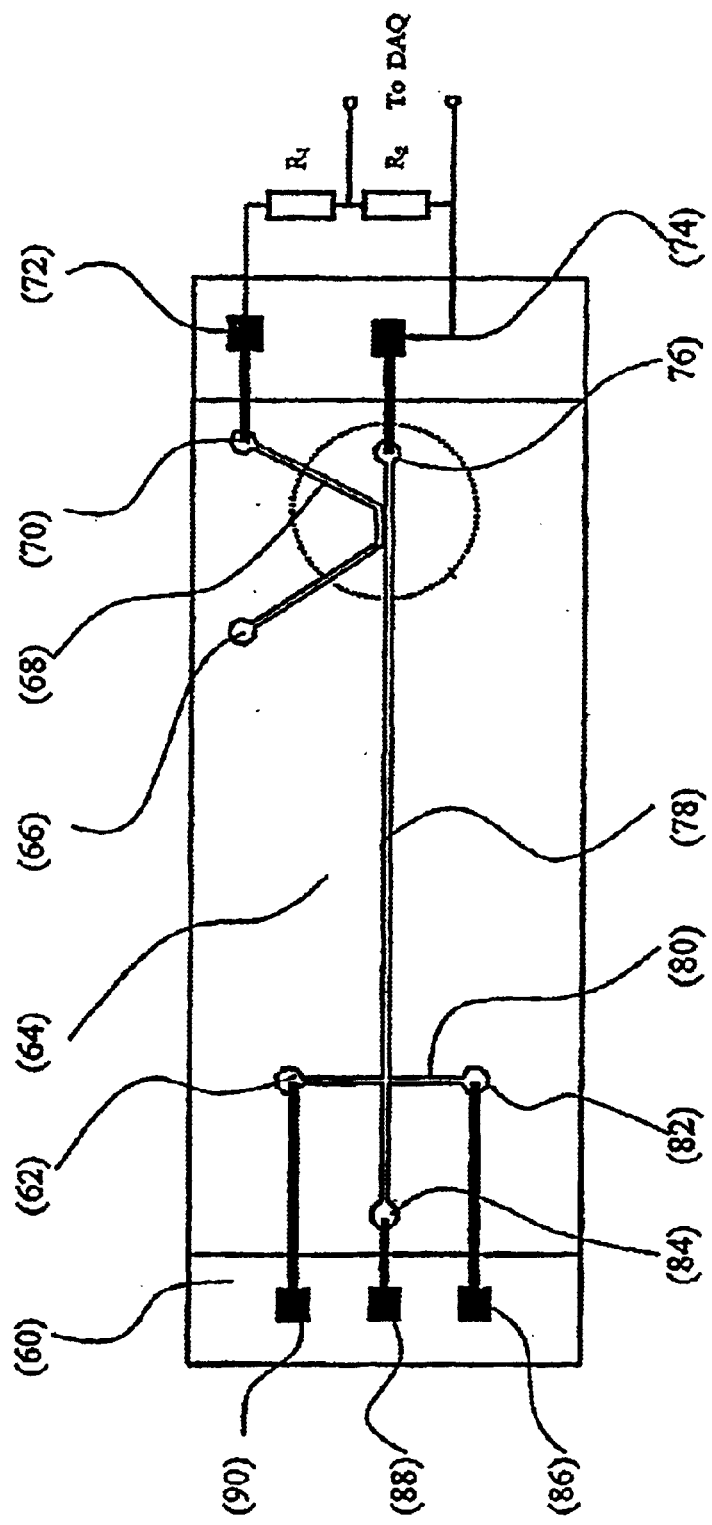
FIG. 4 is a schematic diagram of the microchip CE system to illustrate another embodiment of the invention.
Figure 5:
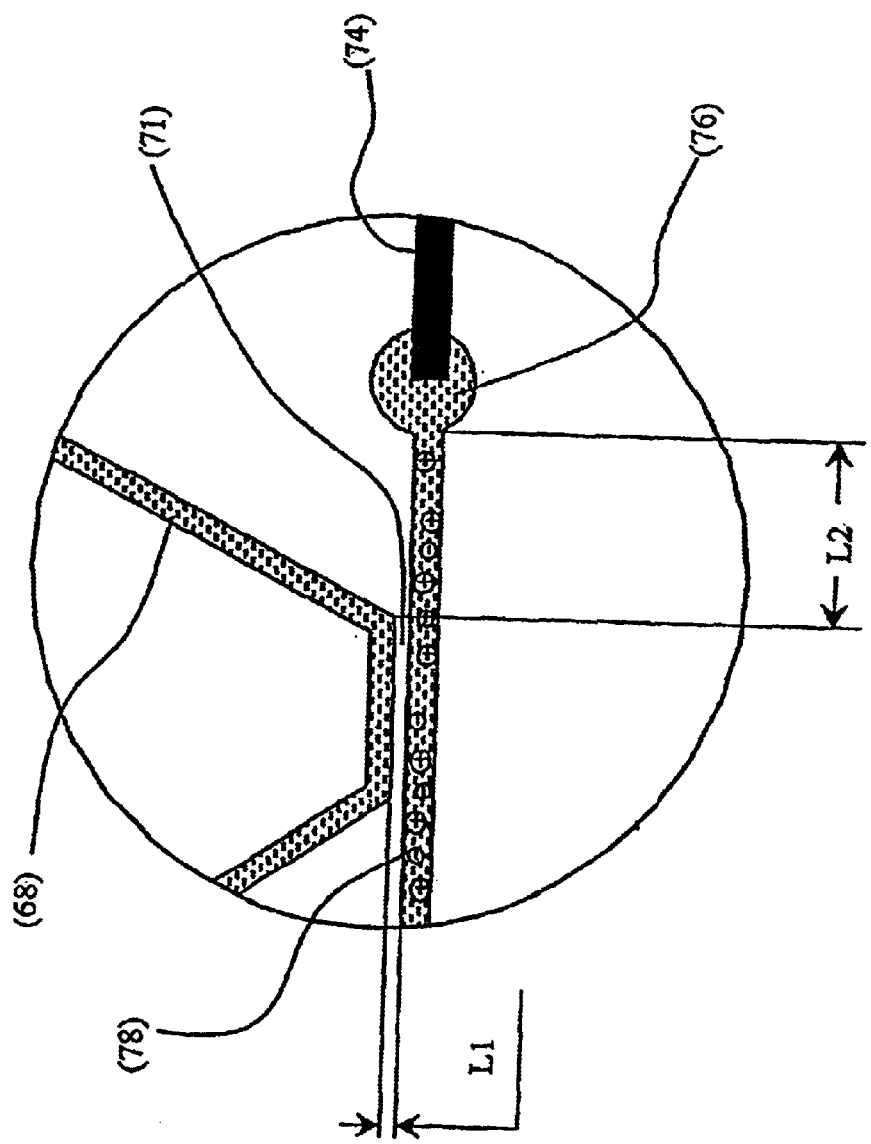
FIG. 5 is an enlarged view of area H as shown in FIG. 4.

A similar design can be used for microchip CE as shown in FIG. 4 and FIG. 5. In this embodiment, only one capillary channel is shown for ease of illustration. It is understood that a CE chip may have numerous channels with various designs. The microchip CE in this example is made of two glass plates 60 and 64. On bottom glass plate 60 is fabricated separation channel 78, injection channel 80 connected to sample reservoir 82 and 62, and sensor channel 68 connected to sensor reservoir 66 and 70. Sample loading electrode 86, waste electrode 90, power electrode 88, sensing electrode 72 and ground/reference electrode 74 are fabricated to connect to sample reservoir 82, waste reservoir 62, inlet reservoir 84, sensor reservoir 70, and outlet reservoir 76 respectively. On the top glass plate, access holes (not shown) are drilled to access the corresponding reservoirs and channels on the glass plate 60. The two glass plates are bonded together during fabrication. The thickness L1 of conductive wall 71 between the detection channel 68 and the separation channel 78 is less than 40 $\mu$m, preferably less than 30 $\mu$m for borate silicate glass. Samples are loaded using the loading and waste electrodes according to standard methods. It has been shown that a thin layer of glass is ion conductive. Based on the same principle described above for CE, sample components in microchip CE can be detected by measuring the potential between the electrodes 72 and 74 during electrophoresis. The distance L2 from the detection channel to the outlet of the separation channel 78 is near or less than the length of the sample plug. For a channel made of glass, this thickness is preferably several tens of micrometers. For microchips made from other types of glass or from other material, the thickness of the conductive wall may be determined by one of ordinary skill in the art without undue experimentation.

Figure 7:
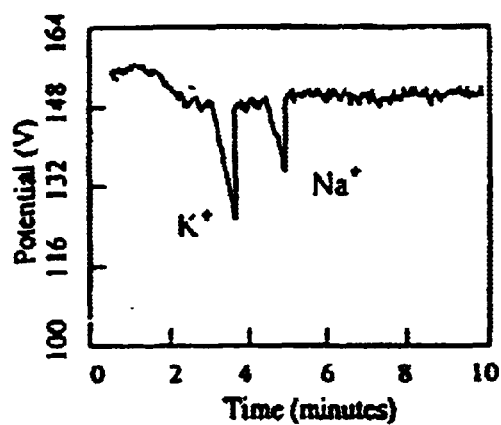
FIG. 7 is an electropherogram obtained using the system shown in FIG. 2A.
Figure 8:
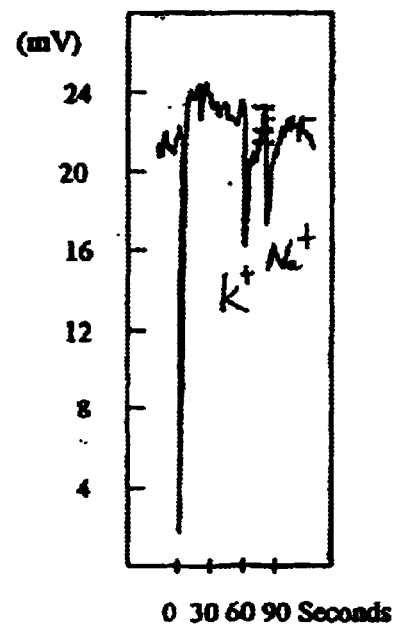
FIG. 8 is an electropherogram obtained on microchip CE using the system shown in FIG. 4.

Experiments have been done in the laboratory to test the feasibility of the present invention. To separate and detect $K^+$ and $Na^+$, 50 mM triethanolamine (pH 6.5, adjusted by adding HCl) was used as running buffer for CE. Platinum electrodes were used for applying high voltages. The sensing electrodes were Ag/AgCl wire (diameter, 1 mm) electrodes. Gigaohm (G$\Omega$) resistors were chosen for the resistors 48 and 50. Data acquisition was obtained through a microprocessor. FIGS. 7 and 8 show typical electropherogram obtained. We can see that $K^+$ and $Na^+$ ions can be well separated and detected using the present invention.

Figure 6:
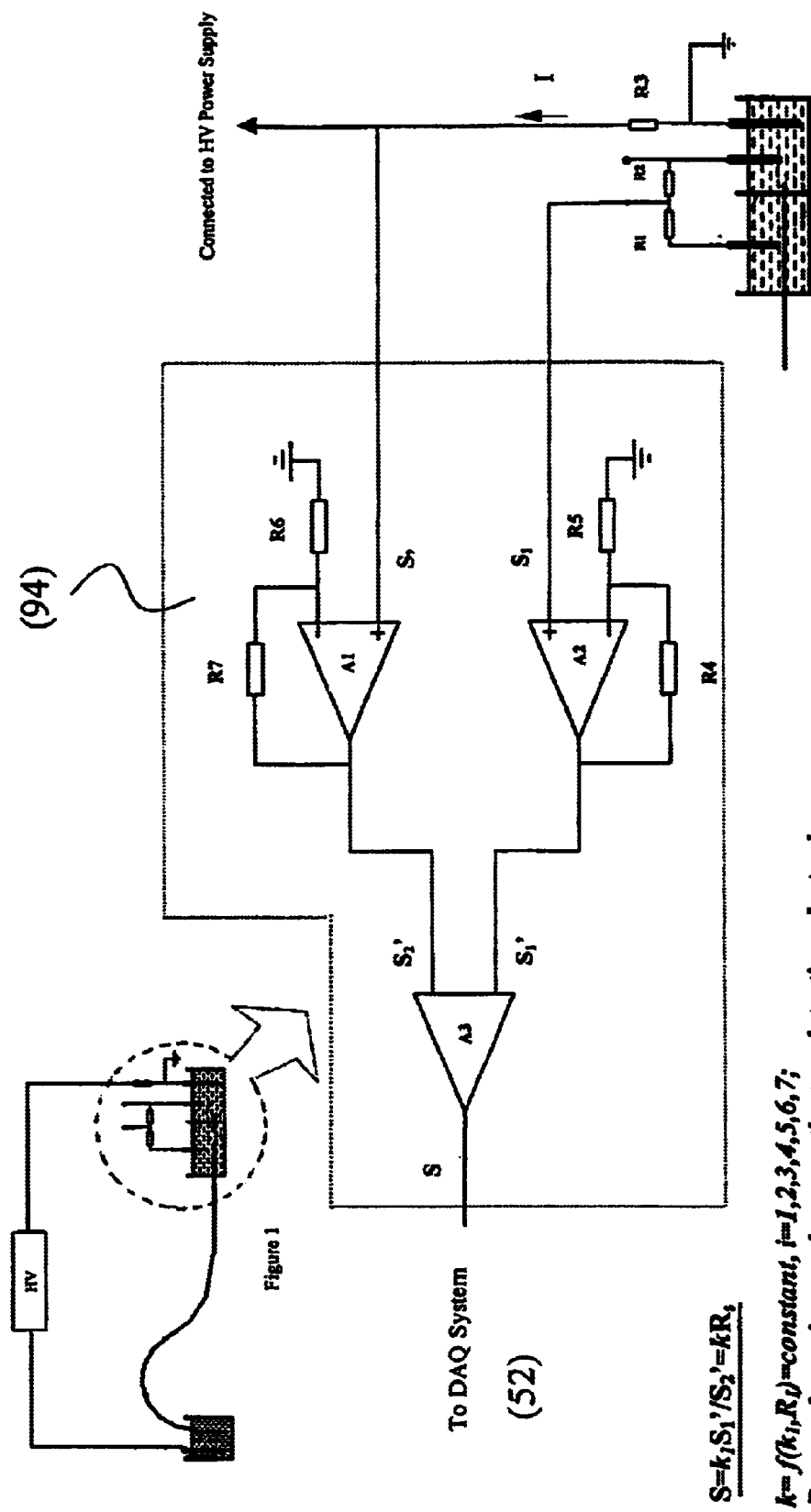
FIG. 6 is a block diagram of a circuit for the detector to illustrate yet another embodiment of the present invention.

From the above explanation, we can expect that noise will exist if high voltage is used for electrophoresis, and the voltage is not stable during electrophoresis, as can be seen in the baselines in FIGS. 7 and 8. To improve signal /noise ratio (S/N), the ratio of the potential measured to the current generated during CE can be measured using a noise reducing circuit 94. One embodiment is shown in FIG. 6. The voltage S1 collected from the sensing electrodes and the voltage S2 due to the current I are amplified by A2 and A1. Then the signal S is obtained by dividing the output S1' from A2 by the output S2' from A1 through a divider A3. From FIG. 6 it can be shown that:

$$I=V/R_0 \qquad (1)$$

$$S_1=I \times R_S \times (R_2/(R_1+R_2)) \qquad (2)$$

$$S_2=I \times R_3 \qquad (3)$$

$$S_1'=S_1 \times (1+R_4/R_5) \qquad (4)$$

$$S_2'=S_2 \times (1+R_7/R_6) \qquad (5)$$

$$S=k_1(S_1'/S_2') \qquad (6)$$

From Eq. 1–6

$$S=k_1(S_1'/S_2')=kR_S \qquad (7)$$

Where k=$k_1 \times \{(1+R_4/R_5) \times R_2\}/[R_3 \times (1+R_7/R_6) \times (R1+R_2)]$= constant From the above results, one can see the signal S is proportional to $R_S$ only and not affected by voltage, current or the resistance of the circuit. In other words, this improved circuit can remove the effects of ripple of the high voltage power supply. Therefore, the baseline noise can be reduced and the ratio of signal to noise will improve.

Those skilled in the art will know that many variations of design can be realized based on the same principle as described above. Although a separate noise reduction circuit 94 is shown in FIG. 6, it should be understood by one skilled in the art that other equivalent interfaces are possible. For instance, the noise reducing function of circuit 94 can be incorporated into a sophisticated data acquisition system 52 as part of its internal submodules.

Figure 9:
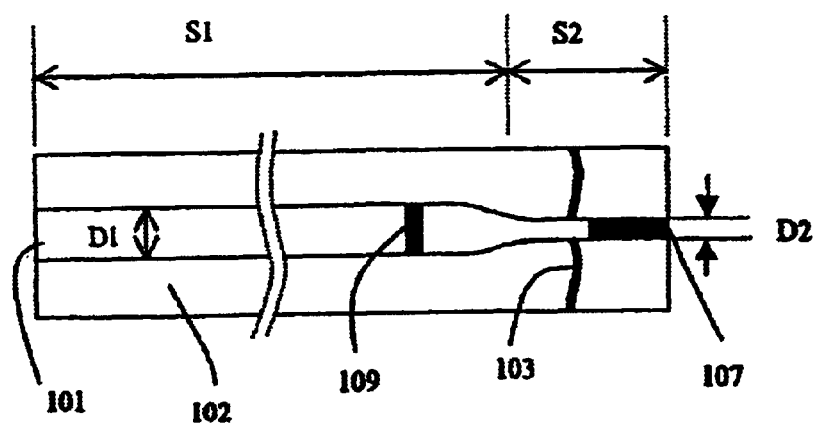
FIG. 9 is a schematic diagram of yet another embodiment of the present invention.

As mentioned above, the distance between the two points where potential difference is measured (e.g. L and L2 in FIG. 2B and 5 respectively) is preferably smaller than the length of the sample plug injected in order to obtain maximum resolution. For capillary electrophoresis, the length of the sample plug Injected is typically around 1 mm. Therefore, L and L2 are preferably less than 1 mm in order to achieve high resolution and sensitivity. Thus good electrical insulation would have to be provided between the two measuring points. Alternatively, a channel with a smaller diameter than that of the separation channel may be provided between the two measuring points such that the distance therebetween may be lengthened without compromising resolution and sensitivity. One example is shown in FIG. 9. In this example, the inlet 101 and outlet ends 107 of a capillary tube 102 is shown. The tube 102 is separated into two parts. Section S1, used for separation, has a larger diameter D1, while section S2, proximate the outlet end in this example, has a smaller inner diameter of D2. A sample 109 of length L3 is shown to migrate from the inlet to the outlet end. As the sample moves towards section S2, the length of the sample would be lengthened due to the smaller diameter of the channel. If the two measuring points for potential gradient detection (which are fracture 103 and the outlet end in this example) is provided at section S2, it is clear that the distance between these two measuring points may also be proportionately lengthened.

Capillaries with varying diameters can be made by normal commercial machines for making capillaries or pulling one end of a capillary tube with uniform diameter to produce one end with a small diameter after heating the tube. Commercially available machines include Laser-based micropipette pullers, for example the P2000 from Sutter Instrument Co. Channels on microchips having varying sizes can be easily produced through different mask design and performing the appropriate photolithography known in the art. The electrically conductive medium contained within the various sensing, outlet and inlet reservoirs may be the same or different, depending on the applications.

Although fused silica and glass substrates are commonly used as separation channels in CE and microchip CE, other substrates, such as poly(dimethylsiloxane) (PDMS) and PMMA, can be used also.

The present invention can be applied to existing electrophoretic channels by providing conductive elements on them, for example, by bonding some filters on them. The bonding method could be, for example, thermal bonding for many plastics, oxygen plasma bonding for PDMS. For a fused silica capillary, well-known techniques such as fracturing, making a frit (U.S. Reissued Pat. 035102) and applying polymers after fracturing (U.S. Pat. No. 5,169,510) may all be applied. For glass channels, a thin wall of 1–40 $\mu$m, preferably 1–20 $\mu$m, may be used. The most effective thickness is dependent on the quality of the glass, and may be determined by one of ordinary skill in the art by routine experimentation.

The detection channel on microchip CE could be on the top or the bottom of the separation channel rather than lying adjacent to the separation channel. The electrodes for sensing can be other electrodes, such as calomel electrode, platinum and gold. The reference electrode In the outlet reservoir can be combined with the ground electrode. For microchip CE, both sensing electrodes and the electrophoresis electrodes can be microfabricated on the chips or just inserted directly in the buffer reservoirs. It is also possible to create two or more conductive elements on the capillary or the separation channel in order to detect sample components at different places. For example, by having two factures along two different points of a capillary tube. The reference electrode may also be positioned away from the outlet end by creating an additional conductive element and the corresponding reservoir for connection to the reference electrode.

What is claimed is:

1. An electrophoretic apparatus comprising:
    a power supply with a ground electrode and a power electrode;
    a separation channel with an inlet end and an outlet end and containing separation medium, said inlet end electrically coupled to the power electrode of said power supply, said outlet end electrically coupled to the ground electrode of said power supply;
    a data acquisition system with a reference electrode and an electrical potential sensing electrode, said reference electrode electrically coupled to said ground electrode; and
    a conductive element, provided on said separation channel between said inlet end and said outlet end, said conductive element permitting electrical signals to pass through without detectable bulk flow of separation medium and sample, said sensing electrode electrically coupled to said conductive element
    whereby the electrical potential within the separation channel between the conductive element and the outlet end may be detected by said data acquisition system without causing disturbance to the flow of samples in said separation channel.

2. An electrophoretic apparatus according to claim 1 further comprising an inlet reservoir connected to said inlet end, said inlet reservoir for retaining electrically conductive medium to which said power electrode is coupled.

3. An electrophoretic apparatus according to claim 1 further comprising an outlet reservoir connected to said outlet end, said outlet reservoir for retaining electrically conductive medium to which said ground electrode is coupled.

4. An electrophoretic apparatus according to claim 1 wherein said conductive element is connected to a sensing reservoir such that said conductive element is electrically connected to said sensing electrode via electrically conductive medium retained within said sensing reservoir.

5. An electrophoretic apparatus according to claim 1 further comprising
    an inlet reservoir connected to said inlet end, said inlet reservoir for retaining said separation medium to which said power electrode is coupled;
    an outlet reservoir connected to said outlet end, said outlet reservoir for retaining said separation medium to which said ground electrode is coupled; and
    a sensing reservoir connected to said conductive element, said sensing reservoir for retaining an electrically conductive medium to which said sensing electrode is coupled.

6. An electrophoretic apparatus according to claim 1 wherein said separation channel is a capillary tube, and said conductive element is a fracture in said capillary tube.

7. An electrophoretic apparatus according to claim 1 wherein said conductive element is 0.1 to 5 mm from the outlet end.

8. An electrophoretic apparatus according to claim 1 wherein said separation channel is a capillary tube, said conductive element is a fracture in said capillary tube 0.1 to 5 mm from the outlet end.

9. An electrophoretic apparatus according to claim 1 wherein a second conductive element connected to a sensor reservoir with electrically conducting medium is provided between said conductive element and said inlet end, and said reference electrode is electrically connected to said second sensor reservoir, such that electrical potential within the separation channel between said first and second conductive element may be detected by said data acquisition system without causing disturbance to the flow of separation medium and samples in said separation channel.

10. An electrophoretic apparatus according to claim 1 further comprising a first resistor coupled between said reference electrode and said data acquisition system, and a second resistor coupled between said sensing electrode and said data acquisition system for sampling the potential difference between the reference and sensing electrodes.

11. An electrophoretic apparatus according to claim 10 further comprising a noise reducing means interposed between said sensing electrode and said data acquisition system for removing the ripple effects of said power supply, said noise reducing means comprising:
- at least a first amplifier connected to the sensing electrode for amplifying the potential difference signal between the sensing and the reference electrodes;
- at least a second amplifying connected to the ground electrode for amplifying current signals therefrom; and
- at least one signal divider having its input coupled to said first amplifier and said second amplifier; the output of said signal divider coupled to said data acquisition system for removing noise from said potential difference and current signals.

12. An electrophoretic apparatus comprising:
- a capillary electrophoresis array chip containing
- a plurality of longitudinally aligned capillary separation channels containing separation medium, each said channel having an inlet end and an outlet end,
- a conductive element provided on each of said separation channels proximate the corresponding outlet end, said conductive element allowing electrical signals to pass through without detectable bulk flow of the separation medium and sample;
- at least one sensor reservoir provided for each said conductive element, said sensor reservoir containing electrically conductive medium and being connected to said conductive element of said separation channel;
- a power supply with
  - a ground electrode coupled to each of said outlet ends; and
  - a power electrode coupled to each of said inlet ends
  for electrophoresis of samples provided within said separation channels; and
- a data acquisition system with
  - at least one reference electrode coupled to each of said outlet ends; and
  - a plurality of electrical potential sensing electrodes each coupled to one sensor reservoir
- whereby electrical potential within said separation channels between said conductive element and said outlet end is measured by said data acquisition system.

13. An electrophoretic apparatus according to claim 12 further comprising
- a sample channel connected to each of said separation channel for receiving and loading a sample, and
- a sample electrode coupled to said sample and said power supply for sample injection.

14. An electrophoretic apparatus according to claim 12 further comprising an inlet reservoir connected to each of said inlet end, said inlet reservoir for retaining separation medium to which said power electrode is coupled.

15. An electrophoretic apparatus according to claim 14 wherein said inlet reservoirs are interconnected.

16. An electrophoretic apparatus according to claim 12 further comprising an outlet reservoir connected to each of said outlet end, said outlet reservoir for retaining separation medium to which said ground electrode is coupled.

17. An electrophoretic apparatus according to claim 16 wherein said outlet reservoirs are interconnected.

18. An electrophoretic apparatus according to claim 12 wherein said conductive element is connected to a sensing reservoir such that said conductive element is electrically connected to said sensing electrode via electrically conductive medium retained within said sensing reservoir.

19. An electrophoretic apparatus according to claim 12 further comprising
- an inlet reservoir connected to each of said inlet end, said inlet reservoir for retaining separation medium to which said power electrode is coupled;
- an outlet reservoir connected to each of said outlet end, said outlet reservoir for retaining said separation medium to which said ground electrode is coupled; and
- a sensing reservoir connected to said conductive element, said sensing reservoir for retaining an electrically conductive medium to which said sensing electrode is coupled.

20. An electrophoretic apparatus according to claim 19 wherein said outlet reservoirs are interconnected.

21. An electrophoretic apparatus according to claim 19 wherein said inlet reservoirs are interconnected.

22. An electrophoretic apparatus according to claim 12 wherein said electrophoretic chip is made of glass, and said conductive element is a thin wall separating said channel and said sensor reservoir, said thin wall being less than 40 $\mu$m thick.

23. An electrophoretic apparatus according to claim 12 wherein said conductive element is less than 5 mm from the outlet end.

24. An electrophoretic apparatus according to claim 12 wherein said conductive element is a thin wall separating said channel and said sensor reservoir, and the length of said conductive element along the longitudinal axis of said channel is less than 10 mm.

25. An electrophoretic apparatus according to claim 12 wherein a second conductive element connected to a second sensor reservoir with electrically conducting medium is provided on said channel between said conductive element and said inlet end, and said reference electrode is electrically connected to said second sensor reservoir, such that electrical potential within the separation channel between said first and second conductive elements may be detected by said data acquisition system without causing disturbance to the flow of separation medium and samples in said separation channel.

26. An electrophoretic apparatus according to claim 12 further comprising
- a sample channel connected to said separation channel for receiving and loading a sample;
- a sample electrode in electrical contact with said sample in said sample channel and coupled to said power supply for sample injection;
- a waste channel connected to said sample reservoir for receiving and retaining excess samples; and a waste electrode in electrical contact with said sample in said waste channel and coupled to said power supply for controlling the sample injection process.

27. A method for detecting samples in an electrophoretic system, said system containing an electrophoretic channel with an inlet end and an outlet end, said channel containing electrophoretic medium and samples, said apparatus further containing an electrically conductive element on the wall of said electrophoretic channel proximate said outlet end, said conductive element permitting electrical signal to pass through without detectable bulk flow of electrophoretic medium and sample, said method comprising:

separating the samples in said electrophoretic channel containing electrophoretic medium by producing an electrical field between the inlet end and the outlet end;

sensing the electrical potential within the channel between the conductive element and the outlet end.

* * * * *